(12) United States Patent
Sakakura et al.

(10) Patent No.: US 7,749,464 B2
(45) Date of Patent: Jul. 6, 2010

(54) PLATE TYPE CATALYTIC REACTOR

(75) Inventors: Yasuyuki Sakakura, Yokkaichi (JP); Youji Kawatani, Yokkaichi (JP); Teruo Saitou, Yokkaichi (JP)

(73) Assignees: Mitsubishi Chemical Corporation, Tokyo (JP); Mitsubishi Chemical Engineering Corporation, Tokyo (JP)

( * ) Notice: Subject to any disclaimer, the term of this patent is extended or adjusted under 35 U.S.C. 154(b) by 617 days.

(21) Appl. No.: 11/141,614

(22) Filed: Jun. 1, 2005

(65) Prior Publication Data
US 2005/0226793 A1  Oct. 13, 2005

Related U.S. Application Data

(63) Continuation of application No. PCT/JP03/15878, filed on Dec. 11, 2003.

(30) Foreign Application Priority Data

Dec. 26, 2002  (JP) .............................. 2002-376639

(51) Int. Cl.
- *B01J 8/02*   (2006.01)
- *B01J 35/02*  (2006.01)
- *B01J 10/00*  (2006.01)
- *B01J 19/00*  (2006.01)
- *B01D 53/34*  (2006.01)
- *F28F 3/00*   (2006.01)
- *F28F 3/14*   (2006.01)
- *F28F 9/02*   (2006.01)

(52) U.S. Cl. ........................ 422/211; 422/168; 422/170; 422/188; 422/190; 422/191; 422/192; 422/193; 422/198; 422/222; 165/166; 165/167; 165/170; 165/173

(58) Field of Classification Search ................. 422/211, 422/188, 190–193, 222, 170, 168, 178, 198; 165/166, 167, 170, 173
See application file for complete search history.

(56) References Cited

U.S. PATENT DOCUMENTS 1,861,292 A * 5/1932 Barrett ........................ 165/117

(Continued)

FOREIGN PATENT DOCUMENTS

EP    1 147 807 A2   10/2001

(Continued)

OTHER PUBLICATIONS

Machine translation of JP 2001-038195 A.*

(Continued)

*Primary Examiner*—Walter D Griffin
*Assistant Examiner*—Natasha Young
(74) *Attorney, Agent, or Firm*—Oblon, Spivak, McClelland, Maier & Neustadt, L.L.P.

(57) ABSTRACT

A plate type catalytic reactor in which components of a starting material gas react comprises a plurality of pairs of heat transfer plates, each pair being formed of two sheets of corrugated plates joined to each other and each pair having a plurality of interior heat transfer medium flow passages, that are arranged so that projected surface parts and recessed surface parts of the corrugated plates of adjacent heat transfer plates are opposed to each other and so that the plurality of pairs of corrugated plates placed in contiguous non-contacting relationship define a plurality of catalyst bed regions in which catalyst material is placed, each having an inlet for the flow of starting gas material and an outlet for the egress of reaction product, wherein the direction of flow of the heat transfer medium through the passages is perpendicular to the direction of flow of starting material gas through the plurality of catalyst regions.

11 Claims, 6 Drawing Sheets

U.S. PATENT DOCUMENTS

| | | | |
|---|---|---|---|
| 4,340,501 A | | 7/1982 | Davidson |
| 5,035,867 A | * | 7/1991 | Dang Vu et al. ............. 422/200 |
| 7,253,308 B1 | * | 8/2007 | Hechler et al. .............. 562/532 |
| 2001/0023761 A1 | * | 9/2001 | Motzet et al. ................ 165/166 |
| 2002/0161243 A1 | * | 10/2002 | Zehner et al. ................ 549/262 |

FOREIGN PATENT DOCUMENTS

| | | | | |
|---|---|---|---|---|
| EP | 1 321 185 A1 | | 6/2003 | |
| JP | 9-508565 | | 9/1997 | |
| JP | 2001-038195 | | 2/2001 | |
| JP | 2001-038195 A | * | 2/2001 | |
| JP | 2001038195 A | * | 2/2001 | |
| JP | 2001-137689 | | 5/2001 | |
| JP | 2001-139499 | | 5/2001 | |
| JP | 2004-167448 | | 6/2004 | |
| WO | WO 91/18668 | | 12/1991 | |
| WO | WO 95/01834 | | 1/1995 | |
| WO | WO 99/29416 | * | 6/1999 | |
| WO | WO 01/32301 | | 5/2001 | |
| WO | WO 01/51448 | | 7/2001 | |

OTHER PUBLICATIONS

English Translation of JP-2001038195 A. The translation has the same publication date as JP-2001038195 A, 2001.*

* cited by examiner

PLATE TYPE CATALYTIC REACTOR

TECHNICAL FIELD

The present invention relates to a plate type catalytic reactor for producing a useful component by transforming a gaseous starting material in a gas phase reaction accompanying heat generation or heat absorption, by using a heterogeneous solid catalyst of pellet or spherical shape. In particular, it relates to a plate type catalytic reactor capable of improving reaction performance and extending the service life of a catalyst wherein the reaction heat generated or absorbed in a catalyst layer having a heterogeneous solid catalyst is removed or supplied for heating by means of a heat transfer medium in the inner space isolated by a heat transfer plate whereby a temperature profile in the catalyst layer can effectively be controlled.

BACKGROUND ART

For the heterogeneous catalytic reaction using a solid catalyst of pellet or spherical shape, a fixed bed reactor or a multi-tube type reactor functioning as a heat exchanger is generally used. The multi-tube type reactor is in particular used for a reaction generating a very large reaction heat and showing a remarkable increase of catalyst temperature (see, for example, JP-A-2001-139499 and JP-A-2001-137689).

These publications disclose, as examples of reaction, the production of an ethylene oxide from ethylene and oxygen, the production of acrolein or an acrylic acid by the oxidation of propylene, the production of methacrolein or a methacrylic acid by the oxidation of isobutylene or tertiary butanol, the production of formalin from methanol and so on.

The catalyst used for these reactions is generally in a spherical or cylindrical shape having a diameter of from 2 to 15 mmΦ, and the reaction tubes of the multi-tube type reactor are generally in a cylindrical shape having an inner diameter of from 20 to 50 mmΦ and a length of from 1 to 5 m. For an industrial purpose, a single reactor has reaction tubes in a number of from several thousands to several ten thousands.

In order to cool or heat the reaction tubes, a heat transfer medium is circulated in a space (at a shell side) defined by the shell (outer shell) of the reactor, surrounding the reaction tubes and a tube plate for fixing the reaction tubes, and a part of the heat transfer medium is discharged and is cooled or heated to be returned repeatedly to the reactor.

As the heat transfer medium, a molten salt such as a nitrate mixture, an organic heat transfer medium containing as the major component a polynuclear aromatic compound, boiled water or a boiled organic medium is generally used.

As an example of a reaction in which absorption of heat in the reaction decreases the temperature of a starting material gas whereby the progress of the reaction is delayed or the ultimate reaction rate decreases, there is known the production of styrene by the dehydrogenation of ethyl benzene.

Conventionally, a fixed bed reactor has been used for such reaction in which a reaction heat is supplied to a starting material gas by supplying a preheated hot gas. A multi-tube type reactor is sometimes used. However, there is restriction on the heat transfer medium to be supplied to the shell side because it is necessary to elevate the temperature to around 600° C.

Such conventional multi-tube type reactor has cylindrical reaction tubes in a number of from several thousands to several ten thousands and a solid catalyst of pellet or spherical shape filled in the reaction tubes, and the control of temperature to the catalyst layer is carried out by supplying a heat transfer medium into the shell at an outer side of the reaction tubes and adjusting the temperature of the heat transfer medium.

When a heterogeneous gas phase reaction is carried out in the multi-tube type reactor, the reaction region in a part of ⅓ from the inlet for a starting material gas in the all reaction regions in the reaction tubes indicates the largest reactivity. FIG. 7 shows the temperature profile in the catalyst layer.

However, the surface area of heat transfer for removing the reaction heat is equal in the all reaction regions because it depends on the outer surface area of the reaction tubes. Further, the temperature at the shell side to which the heat transfer medium was introduced was contrived to have a uniform temperature as possible, and the supply of the heat transfer medium and the flow pattern of it were contrived so as to keep the same medium temperature on a plane perpendicular to the reaction tubes whereby reactions occurred at the same temperature in the almost reaction tubes. Accordingly, with respect to the removal of reaction heat or the application of heat over the all reaction regions, the reaction regions of the reaction tubes are according to the same design.

However, the temperature profile in a catalyst layer in a reaction tube is such that in the reaction region in the vicinity of the inlet of reaction tube where the reactivity is large, the removal of heat generated by the reaction is insufficient and the heat is accumulated in the catalyst layer to elevate the temperature of the catalyst layer. In the extreme case, the catalyst is damaged due to a high temperature. This phenomenon is called "a hot spot".

In a case of oxidation reaction accompanying an extremely large heat, there was the problem that the temperature of the catalyst layer was very high in, in particular, the reaction region in the vicinity of the catalyst layer inlet, hence, a hot spot being easily formed. The hot spot in the catalyst layer elevates the temperature at the surface of the catalyst to accelerate the deterioration of the catalyst in this reaction region and reduces the selectivity of reaction, whereby the yield of the product decreased.

In order to avoid the hot spot, an improving method such that temperature profiles in catalyst layers in reaction tubes are equalized, has conventionally been proposed. For example, as a method for obtaining a good reaction performance and a high yield, there is proposed an improvement that a plurality of inlets are provided for a heat transfer medium supplied to the shell side of the reactor, and the heat transfer medium is supplied with different temperatures so that the heat transfer medium is controlled to have different temperatures at positions along the axial direction of the reaction tubes.

In order to supply the heat transfer medium having different temperatures from different positions of the reaction tubes, however, it is necessary to provide the same number of heat transfer medium supply equipments as the different temperatures on the heat transfer medium. Further, it is difficult to mix quickly at the shell side the supplied heat transfer medium having different temperatures with the heat transfer medium circulated in the reactor. This brings further non-uniformity of the heat transfer medium temperature at the shell side of the reactor.

On the other hand, there is a method that plural kinds of catalysts are filled in a reaction tube or a catalyst is mixed with an inert dilution agent so as to control the reactivity in the reaction region at the inlet.

This method is to control the temperature of the catalyst layer by controlling the reaction heat generated in or drawn from the reaction region in the vicinity of the inlet. However, in the case of using an industrial reactor having reaction tubes in a number of several thousands to several ten thousands, plural kinds of catalysts have to be uniformly filled in reaction regions of reaction tubes while adjusting the activity of the catalysts, or in using a dilution agent, mixtures of plural kinds of catalysts and the dilution agent have to be uniformly filled in the reaction tubes. When the catalysts in the reaction tube are to be replaced by new ones, much labor and a long time are needed to replace the catalysts. During the replacement the reaction has to be stopped.

Further, when the activity of reaction has to be adjusted by using a catalyst having a low reaction activity or by diluting a catalyst with an inert material, a larger amount of catalyst than originally intended has to be filled in reaction tubes, or an inert material which is basically unnecessary has to be filled in reaction regions. This caused a large pressure loss in a starting material gas passed through the catalyst layer. In particular, in an oxidation reaction, there was the problem of increasing power for a blower or a compressor necessary to compress molecular oxygen-containing gas such as air.

It is an object of the present invention to provide a new plate type catalytic reactor in which a temperature increase in a catalyst layer can be suppressed to prevent the formation of a hot spot and to prevent the deterioration of the catalyst filled in the catalyst layer whereby the service life of the catalyst can be prolonged; the optimum selectivity of reaction is attainable, and a pressure loss increase in a starting material gas passed through the catalyst layer can be prevented, in employing a heterogeneous gas phase reaction method using a solid catalyst of pellet or spherical shape.

DISCLOSURE OF THE INVENTION

The present invention relates to a new plate type catalytic reactor to solve the above-mentioned problems, and it has the following features.

(1) A plate type catalytic reactor characterized in that a plurality of pairs of heat transfer plates, each formed of two sheets of corrugated plates joined to each other and each having a plurality of heat transfer medium flow passages, are arranged so that projected surface parts and recessed surface parts of the corrugated plates of adjacent heat transfer plates are opposed to each other to form a catalyst layer.

(2) The plate type catalytic reactor according to the above-mentioned (1), wherein a circular or elliptic arc shape formed in the corrugated palates is changed to increase the thickness of the catalyst layer from the inlet toward the outlet for a starting material gas fed to the catalyst layer.

(3) The plate type catalytic reactor according to the above-mentioned (1) of (2), wherein the heat transfer medium is fed so as to form a cross flow with respect to the starting material gas.

(4) The plate type catalytic reactor according to the above-mentioned (1) or (2), wherein a plurality of corrugated heat transfer plates are arranged in a radial pattern, the starting material gas is fed from the inner side to the outer side of the catalyst layer, and the heat transfer medium is fed into the flow passages of the corrugated heat transfer plates so as to form a cross flow with respect to the starting material gas.

(5) The plate type catalytic reactor according to any one of the above-mentioned (1) to (4), wherein the heat transfer medium flow passages of the corrugated heat transfer plates are arranged to extend vertically so that the heat transfer medium supplied from the downward flows upward and at least a portion of the heat transfer medium is boiled in the heat transfer medium flow passages.

(6) The plate type catalytic reactor according to any one of the above-mentioned (1) to (5), wherein propylene or isobutylene is oxidized by using a molecular oxygen-containing gas to produce (meth)acrolein and (meth)acrylic acid, or (meth)acrylic acid is produced from (meth)acrolein by using a molecular oxygen-containing gas.

EXPLANATION OF REFERENCE NUMERALS

Figure 1:
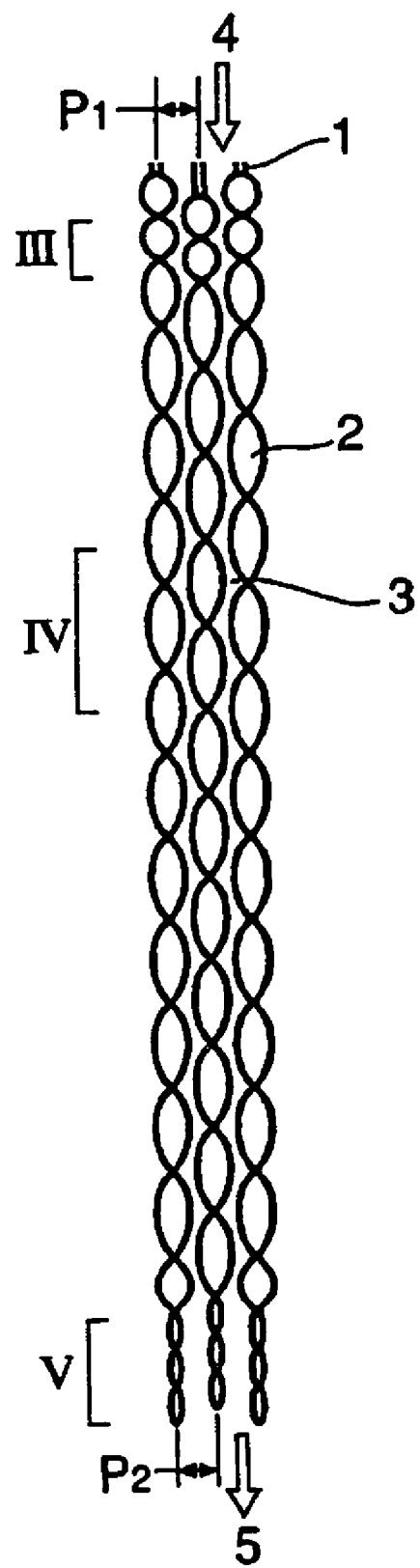
FIG. 1 is a longitudinal cross-sectional view of heat transfer plates placed in the plate type catalytic reactor of the present invention.

1 . . . heat transfer plate
2 . . . heat transfer medium flow passage
3 . . . catalyst layer
4 . . . reaction gas inlet
5 . . . reaction gas outlet
6 . . . heat transfer medium supply port
11 . . . corrugated plate
a . . . projected surface part of corrugated plate
b . . . recessed surface part of corrugated plate
$S_1, S_2, S_3$ . . . throat for starting material as

BEST MODE FOR CARRYING OUT THE INVENTION

The plate type catalytic reactor used in the present invention is a plate type catalytic reactor comprising a pair of heat transfer plates each formed by joining projected surface parts of two corrugates plates to form a plurality of heat transfer medium flow passages and a catalyst layer between adjacent heat transfer plates which are arranged in a plurality of pairs with a predetermined space therebetween.

A starting material gas supplied into the plate type catalytic reactor is passed along outer sides of the heat transfer plates and the heat transfer medium is supplied into the inner side of the paired heat transfer plates. The flow direction of the heat transfer medium is perpendicular to the flow of the starting material gas, i.e., is in a direction to the cross current flow.

The space between a pair of heat transfer plates and an adjacent pair of heat transfer plates, i.e., the thickness of the catalyst layer (catalyst layer thickness) to be filled therebetween has a distance in a direction perpendicular to the flow of the starting material gas. The space between the paired heat transfer plates and the adjacent paired heat transfer plates may be changed depending on reactivity.

The reactivity in a normal reaction is largest at the inlet portion of starting material gas at which the reaction heat generated in the reaction is the largest, and it decreases toward the outlet of starting material gas. In a case of an endothermal reaction as the dehydrogenation of ethyl benzene, the catalyst layer is heated by a heat transfer medium to accelerate the reaction conversion rate. In order to remove the reaction heat or utilize the reaction heat efficiently, the projected or recessed shape of corrugated plates used for a heat transfer plate and an adjacent heat transfer plate is changed whereby the space between adjacent heat transfer plates is adjusted, in other words, the catalyst layer thickness is changed to control the reaction, so that the temperature of the catalyst layer can be controlled.

In the following, the plate type catalytic reactor of the present invention will be described with reference to the accompanying drawings.

FIG. 1 is a longitudinal cross-sectional view of heat transfer plates placed in the plate type catalytic reactor of the present invention.

Figure 2:
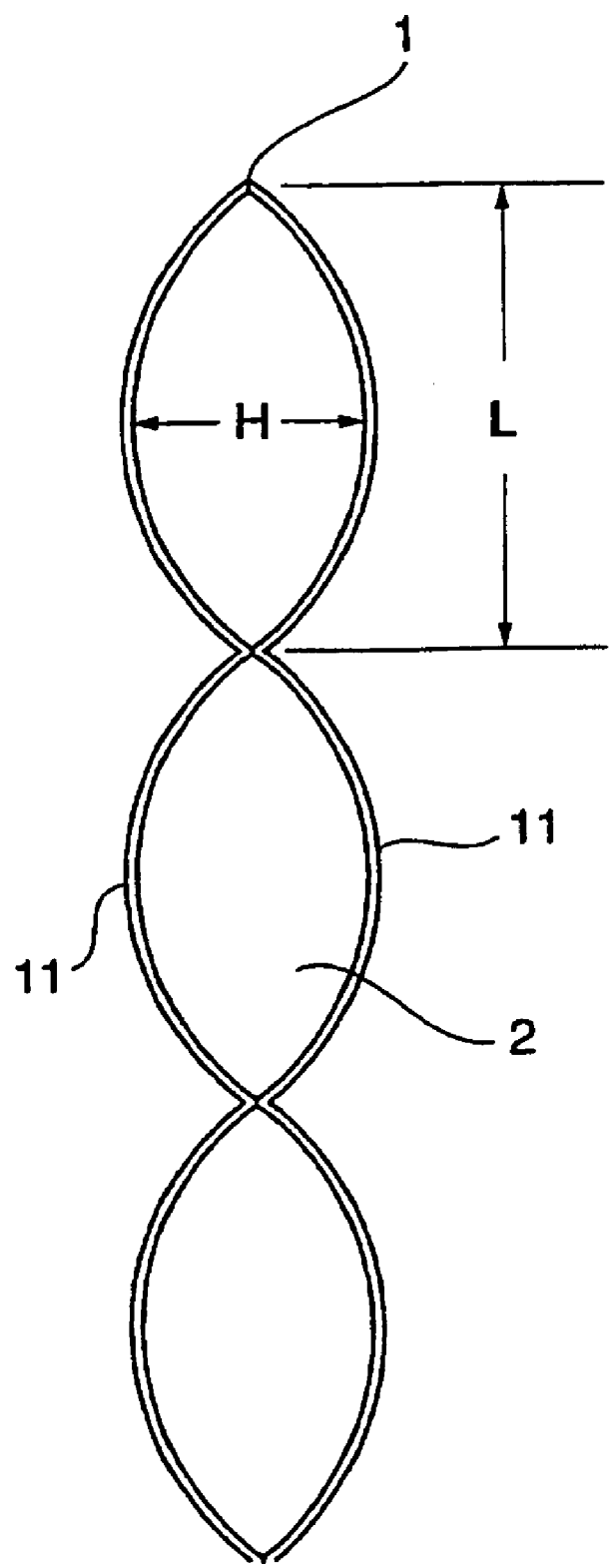
FIG. 2 is an enlarged view of a heat transfer plate formed by joining two corrugated plates.

FIG. 2 is an enlarged view of a heat transfer plate formed by joining two corrugated plates.

Figure 3:
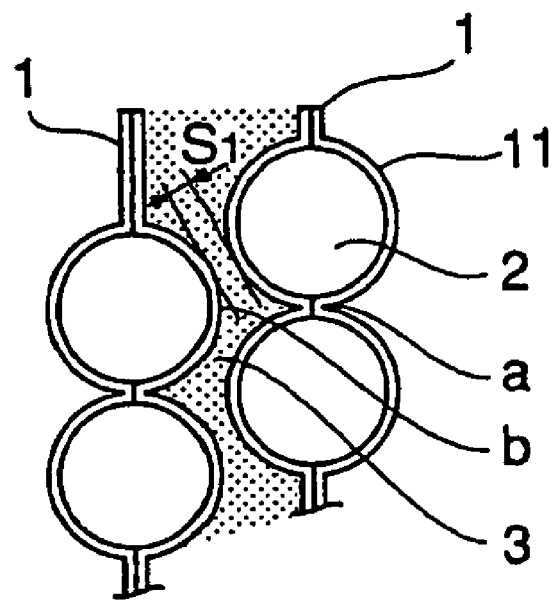
FIG. 3 is an enlarged view of a part III in FIG. 1
Figure 4:
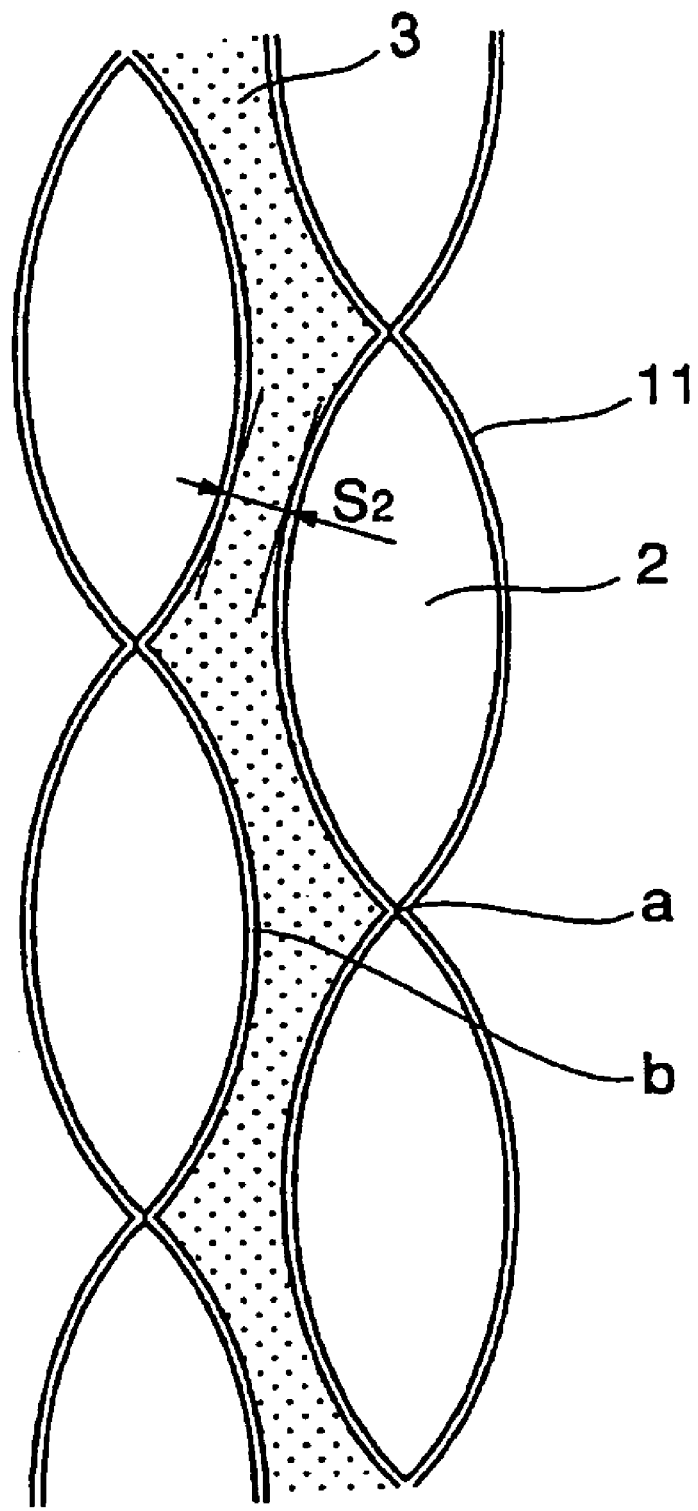
FIG. 4 is an enlarged view of a part IV in FIG. 1.
Figure 5:
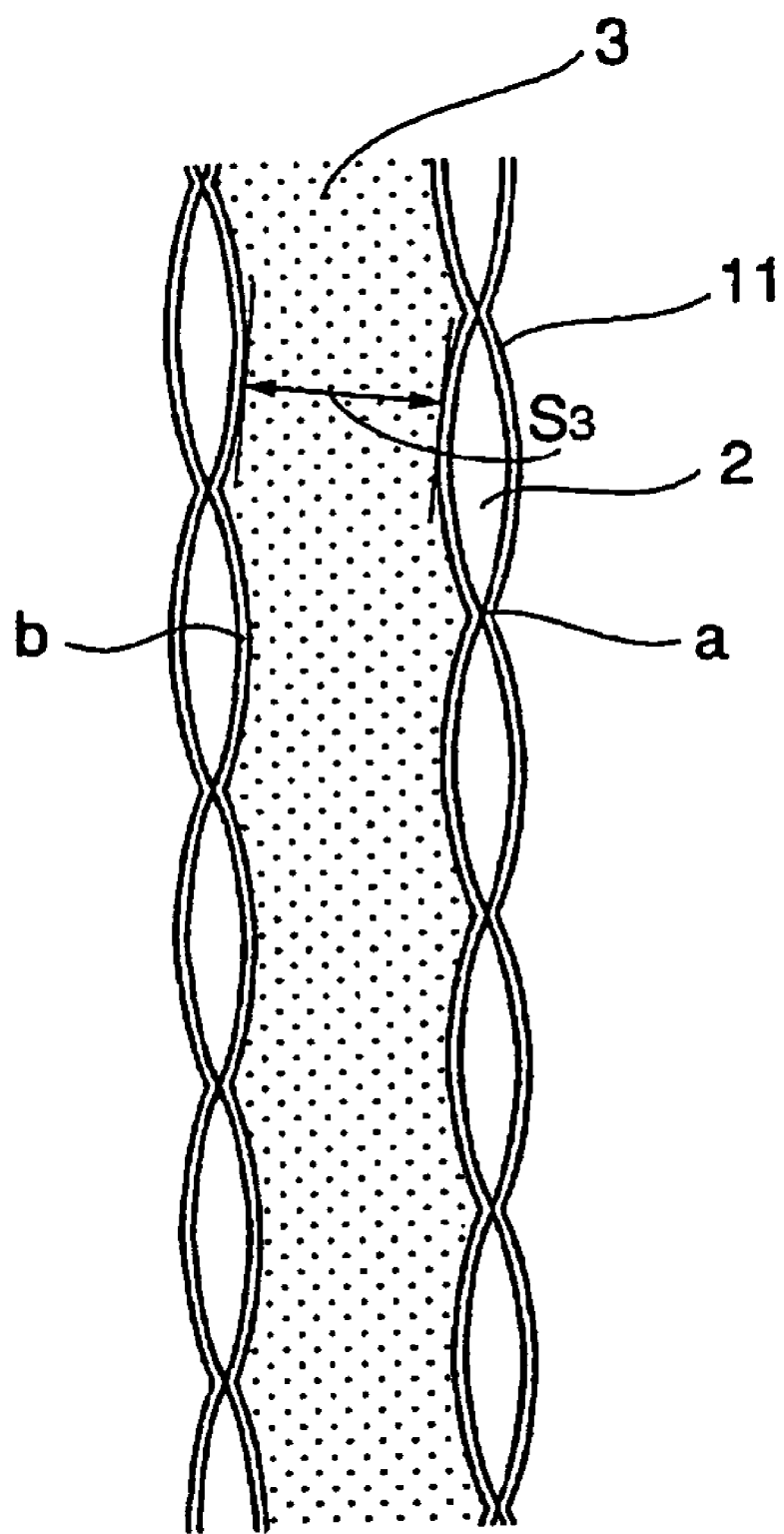
FIG. 5 is an enlarged view of a part V in FIG. 1.
Figure 6:
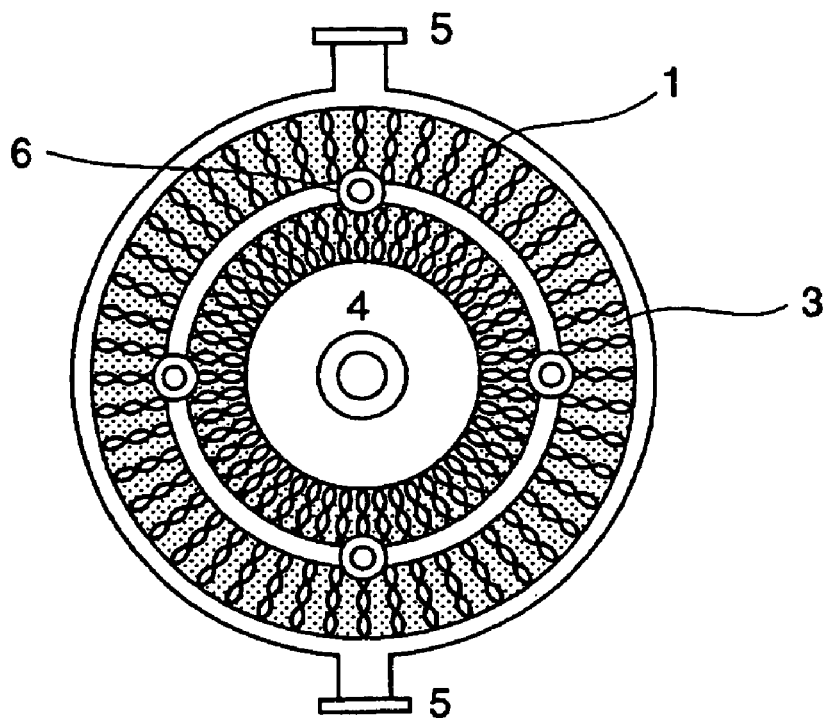
FIG. 6 is a cross-sectional view of a plate-type catalyst reactor having heat transfer plates arranged radially.
Figure 7:
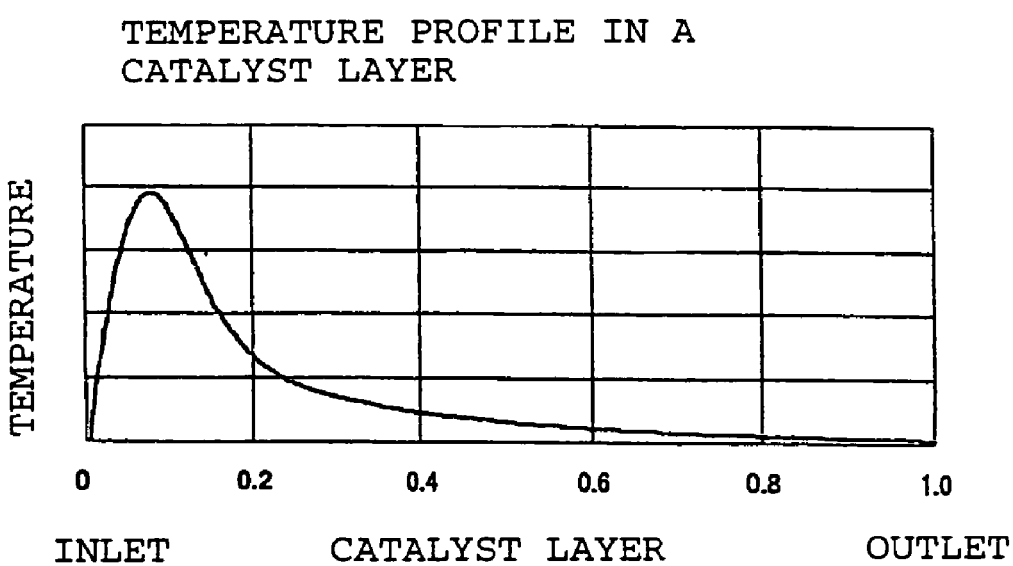
FIG. 7 is a diagram of temperature profile in a catalyst layer in a conventional multi-tube type reactor.

FIG. 3 is an enlarged view of a part III in FIG. 1
FIG. 4 is an enlarged view of a part IV in FIG. 1
FIG. 5 is an enlarged view of a part V in FIG. 1
FIG. 6 is a cross-sectional view of a plate type catalytic reactor having heat transfer plates arranged radially.

In FIG. 1, numeral 1 designates a heat transfer plate formed by opposing two corrugated plates, numeral 2 designates a heat transfer medium flow passage formed inside the heat transfer plate 1 and numeral 3 designates a catalyst layer in which a catalyst is filled, the catalyst layer being defined by adjacent heat transfer plates 1.

A starting material gas is supplied from a reaction gas inlet 4 to be passed through the catalyst layer 3 during which an intended product is produced. Then, the starting material gas is discharged outside the plate type catalytic reactor through a reaction gas outlet 5.

The flowing direction of the starting material gas is not in particular limited. However, a downward flow or an upward flow is generally determined as shown in the embodiment of the present invention.

The heat transfer medium is supplied into a large number of heat transfer medium flow passages 2 formed in the heat transfer plate so as to flow in a direction to form a cross current flow with respect to the flow direction of the starting material gas. During the flow, the heat transfer medium cools the catalyst layer 3 through the heat transfer plate 1 to remove the reaction heat in the case of an exothermal reaction, or in a case of an endothermal reaction, it heats the catalyst layer 3 and is discharged to the outside of the plate type catalytic reactor.

In the following, the structure of the heat transfer plate 1 will be described in more detail with reference to FIGS. 2 to 6.

FIG. 2 shows a heat transfer plate 1 formed by joining two sheets of corrugated plates 11 wherein the corrugated shape consists of a series of arcs. However, the shape may be determined in consideration of manufacturing or the flow of the starting material gas. Further, the height of corrugation H and the period of corrugation L are not in particularly limited. However, it is appropriate that the height H is from 5 to 50 mm and the period L is from 50 to 200 mm. Specifically, they are determined depending on the reaction heat in a reaction in the catalyst layer 3 and the flow rate of the heat transfer medium used for removing heat or applying heat.

When the heat transfer medium is liquid, the flow rate of the heat transfer medium in the heat transfer medium flow passages 2 is adjusted to have a flow velocity of from 0.1 to 5 m/s. If the flow velocity is low, the resistance to the heat transfer of the heat transfer medium increases to reduce the heat efficiency. If the linear velocity of the heat transfer medium is too large, the pressure of the heat transfer medium increases so that the load of a supply pump becomes large.

FIG. 3 shows the shape of a pair of heat transfer plates 1 at their portions in the vicinity of the inlet for the starting material gas wherein each heat transfer plate 1 is formed by opposing two sheets of corrugated plates 11 having arc portions and by joining opposing projected surface parts a of the corrugated plates 11 to form a plurality of heat transfer medium flow passages 2.

One heat transfer plate 1 and the other heat transfer plate 1 are opposed so that projected surface parts a and recessed surface parts b of corrugated plates of these heat transfer plates are opposed with predetermined spaces whereby the catalyst layer 3 can be formed and throats $S_1$ for the starting material gas can be formed. A required thickness of the catalyst layer 3 and a required throat $S_1$ for the starting material gas can be obtained by changing appropriately the shape of the arc of the corrugated plates 11.

FIG. 4 shows the shape of a pair of heat transfer plates 1 at their intermediate portions of starting material gas flow passages wherein a plurality of heat transfer medium flow passages 2 are formed by opposing two sheets of corrugated plates 11 having elliptic arc portions and by joining projected surface parts a of the corrugated plates 11.

One heat transfer plate 1 and the other adjacent heat transfer plate 1 are opposed so that projected surface parts a and recessed surface parts b of the corrugates plates are opposed with predetermined spaces whereby a catalyst layer 3 can be formed and throats $S_2$ for the starting material gas can be formed. In the same manner as FIG. 3, a required thickness of the catalyst layer 3 and the throat $S_2$ for the starting material gas at a predetermined position can be obtained by changing appropriately the elliptic arc shape of the corrugated plates. In this case, the thickness of the catalyst layer 3 and the throat $S_2$ at this portion are determined to have larger dimensions than those in FIG. 3.

FIG. 5 shows the shape of a pair of heat transfer plates 1 at their portions in the vicinity of the outlet for the starting material gas wherein in each heat transfer plate, a plurality of heat transfer medium flow passages 2 are formed by opposing two sheets of corrugates plates 11 having a series of elliptic arc portions whose height of corrugation H and the period of corrugation L are far shorter than those shown in FIG. 4, and by joining projected surface portions a of the corrugated plates 11.

One heat transfer plate 1 and the adjacent heat transfer plate 1 are opposed so that projected surface parts a and recessed surface parts b of the corrugated plates are opposed with predetermined spaces to thereby form a catalyst layer 3 and throats $S_3$ for the starting material gas. A requires thickness of the catalyst layer 3 and a required throat $S_3$ for the starting material gas at this position can be obtained by changing appropriately the elliptic arc shape of the corrugated plates 11 in the same manner as FIG. 4. The thickness of the catalyst layer 3 and the dimension of the throat $S_3$ at this portion are determined to have further larger dimensions than those in FIG. 4.

FIG. 6 shows an embodiment of the reactor wherein a compact equipment can be obtained by arranging radially a large number of reaction regions surrounded by corrugated heat transfer plates 1, in which catalyst layers 3 filled in the reaction regions extend vertically.

The starting material gas is supplied from the reaction gas inlet 4 at the center of the plate type catalytic reactor to be passed through the catalyst layers 3 in a radial direction, and the starting material gas is passed through the outermost shell portion of the plate type catalytic reactor to be discharged to the outside of the reactor through reaction gas outlets 5.

The temperature-controlled heat transfer medium is passed through supply ports 6 to be distributed to the heat transfer medium flow passages in each heat transfer plate 1 through distribution pipes. Then, the heat transfer medium which has exchanged heat with the reaction heat generated in the catalyst layer 3 is discharged from a heat transfer medium outlet (not shown) through a liquid collection pipe.

The case shown in FIG. 6 is preferably applied when the heat transfer medium causes a phase change due to the boiling or condensation. At this moment, temperatures at the inlet and outlet of the heat transfer medium become the temperature of boiling or condensation. Accordingly, the temperature difference between the inlet and the outlet of the heat transfer medium is minimized whereby it is possible to control equally the temperature of the catalyst layers 3.

When water vapor is used as the heat transfer medium to heat the catalyst layer 3 so that the reaction is accelerated, the heating temperature exceeds 100° C. in most cases whereby a high pressure may be applied. At this moment, the pressure of the water vapor becomes higher than that of the catalyst layer 3. Accordingly, the heat transfer plate 1 has to be designed so as to withstand the pressure difference between the heat transfer medium flow passages and the catalyst layer.

When the temperature of the water vapor is 200° C., the pressure of the water vapor becomes at least 1.5 MPa. Accordingly, the corrugated heat transfer plate 1 has to be designed to have a withstanding pressure of 1.5 MPa. When the corrugated heat transfer plate of the present invention is used, it is possible to improve the withstanding pressure of the heat transfer plate without increasing the thickness of the plate.

The same measures are also applicable to the case of boiling the heat transfer medium when the temperature of the catalyst layer 3 is controlled by heat exchanging the reaction heat by means of the heat transfer medium. In this case, water or an organic liquid having an appropriate boiling point is employed as the heat transfer medium. When water is employed as the heat transfer medium, the pressure of boiled water is about 40 MPa at 250° C. Since the pressure of boiled water increases rapidly at a temperature exceeding this, an organic heat transfer medium is preferably used.

The organic heat transfer medium is not in particular limited in its kind. However, the heat transfer medium is subjected to a temperature of at least 200° C. Accordingly, it is preferred to select the organic heat transfer medium not to cause deterioration due to a low-molecular-weight compound by the decomposition of organic molecules at a high temperature.

In FIG. 6 showing the reactor wherein the corrugated heat transfer plates are arranged in a radial pattern in a vertical direction, the thickness of each catalyst layer is gradually changed from the central portion at which the reaction gas inlet is formed toward an outer peripheral portion. However, the change of the catalyst layer thickness depends on a degree of reaction heat generated. Accordingly, the catalyst layer thickness can be changed by adjusting the height of corrugation H and the period of corrugation L shown in FIG. 2.

In FIG. 1, the pitch $P_1$ between a heat transfer plate and an adjacent heat transfer plate 1 at the position of the reaction gas inlet 4 is identical with the pitch $P_2$ at the position of the reaction gas outlet 5. Namely, the heat transfer plates adjacent to each other are arranged in parallel to each other in a plurality of pairs.

Further, in FIG. 1, a plate type catalytic reactor having a heat transfer plate of a double-length size wherein a corrugated pattern of from the part III to the part V is repeated twice, may be used.

The flow rate of the heat transfer medium is determined depending on the quantity of a reaction heat and the resistance to heat transfer. However, the resistance to heat transfer normally occurs on the side of the starting material gas in a gaseous state rather than the heat transfer medium as liquid. The linear velocity of the liquid in the heat transfer medium flow passages is preferably at least 0.3 m/s.

The most appropriate value is from 0.5 to 1.0 m/s when the resistance at the side of the liquid heat transfer medium is small in comparison with the resistance to heat transfer at the side of the starting material gas. If the value is too large, the capacity of a pump for circulating the heat transfer medium becomes large, such being undesirable in an economical viewpoint.

In the present invention, in order to control appropriately the temperature of the catalyst layer, the difference of temperature at the inlet and the outlet of the heat transfer medium is very important. The flow rate of the heat transfer medium is determined depending on a necessary temperature difference between the inlet and the outlet of the heat transfer medium. The flow rate of the heat transfer medium is determined so that the difference between the inlet temperature and the outlet temperature is from about 0.5 to 10° C., preferably from 2 to 5° C.

A large flow rate of the heat transfer medium reduces the temperature difference. However, large-sized pumps and heat exchanger are needed for the heat transfer medium, and accordingly, it is disadvantageous economically. If the flow rate is too small, the difference between the inlet temperature and the outlet temperature becomes large whereby the temperature of the reaction near the inlet of heat transfer medium differs from the temperature of reaction at the outlet. Accordingly, there creates the problem that the temperature of the catalyst layer is not uniform. Thus, the shape in cross section of the reactor is determined so that a necessary flow rate and a necessary linear velocity can be satisfied for the heat transfer medium flow passages of the plate type catalytic reactor.

A pump is commonly used to circulate the heat transfer medium. The heat transfer medium is subjected to temperature control by using a heat exchanger or mixing a medium having a different temperature, and then, is supplied into corrugated heat transfer medium flow passages 2 of the catalytic reactor.

The reaction heat is exchanged between the heat transfer medium and the catalyst layer 3 through the heat transfer plates 1, and the heat transfer medium is returned to the circulation pump after having been discharged from the catalytic reactor. In the circulation system for the heat transfer medium, a heat transfer medium storage may be provided. The pressure of the heat transfer medium in the heat transfer medium flow passages 2 depends mainly on a rated discharge pressure of a heat transfer medium pump, and the thickness of each heat transfer plate 1 depends on a pressure difference between the heat transfer medium and the catalyst layer 3.

When a flat plate is used for the heat transfer plates 1, it is necessary to use a metal plate having a thickness necessary for withstanding the pressure of the heat transfer medium. In the present invention, heat transfer plates 1 are joined in parallel with a predetermined space. Accordingly, it is possible to use a thin metal plate. Specifically, it is possible for the heat transfer plate 1 to use a metal plate having a thickness of not more than 2 mm, preferably, not more than 1 mm even when the pressure of the heat transfer medium is about 3 MPa.

For the heat transfer plate 1, a thin rectangular metal plate is commonly used. There is no restriction on the dimension in a direction perpendicular to the flowing direction of the starting material gas. If the dimension in the flowing direction of the starting material gas is too long, the pressure loss of the catalyst layer becomes large, hence, the power of the blower or compressor for the starting material gas becomes large, such being disadvantageous economically.

When a chemical product is manufactured in an industrial scale, the length of the catalyst layer in the flowing direction of the starting material gas is preferably from 1 to 5 m in the same manner as the case of the multi-tube type reactor. The total amount of a catalyst filled in a plate type catalytic reactor in order to obtain an intended productivity is determined depending on a reaction rate and a concentration of components in the starting material gas, and accordingly, the amount varies depending on a plate type catalytic reactor used.

The largest amount of the catalyst to be filled between a pair of heat transfer plates 1 varies depending on reactivity and characteristics of the catalyst. However, the amount of catalyst is up to 5 $m^3$, preferably, not more than 2 $m^3$ in consideration of the shape of heat transfer plate 1 from an economical viewpoint.

The shape of the catalyst to be filled is generally spherical, columnar or is in a Rashig-ring shape. The particle diameter is from 3 to 20 mmΦ in many cases. The smallest distance $S_1$, $S_2$, or $S_3$ between a heat transfer plate 1 and an adjacent heat transfer plate 1 varies depending on the particle diameter of a usable catalyst. Usually, the smallest distance should be at least 1.5 times of the particle diameter of the catalyst.

Specifically, it is determined that $S_1$ as the distance between heat transfer plates at the inlet for the starting material gas is from 5 to 20 mm, $S_2$ at an intermediate portion of the catalyst layer is from 10 to 30 mm and $S_3$ at a position in the vicinity of the outlet for the starting material gas is from about 20 to 50 mm. Preferably, $S_1$=10 to 15 mm, $S_2$=15 to 20 mm and $S_3$=30 to 40 mm are selected.

Respective distances S formed between heat transfer plates each vary depending on a degree of reactivity. The distances may be changed continuously or stepwise from the inlet to the outlet of the catalyst layer 3. However, in consideration of non-uniformity of reactivity of a catalyst to be manufactured, it would be better to change stepwise the distances S between the heat transfer plates 1 because flexibility can be obtained.

It is proper to divide reaction regions into a number of from 2 to 5 in stage. Further, in determining properly the length of each region, an $S_1$ portion is from $\frac{1}{10}$ to $\frac{1}{3}$, an $S_2$ portion is from $\frac{1}{5}$ to $\frac{1}{3}$ and an $S_3$ portion is from $\frac{1}{4}$ to $\frac{1}{2}$ with respect to the entire length of the catalyst layer. However, the length of the catalyst layer at the $S_3$ portion varies depending on the achievement of the conversion rate of reaction.

When a preheat zone is provided for the starting material gas in front of the inlet of the catalyst layer 3, it is added to the length of the catalyst layer at the $S_1$ portion.

Changes of the thickness of the catalyst layer from the inlet to the outlet of the starting material gas in its flowing direction can not straightly be determined. It is because the changes should be determined by reactive factors such as the reaction rate, the ultimate conversion rate at the outlet, reaction heat in a reaction including a side reaction and so on, heat transfer factors such as the temperature and flow rate of the heat transfer medium, the flow rate of the starting material gas, the heat transfer coefficient relating to removal of heat/application of heat, the heat capacity and so on, and factors related to the catalyst such as the allowable temperature not to cause the damage of the catalyst, the temperature preventing the deterioration of the catalyst and so on.

Ideally, the changes of the thickness of the catalyst layer should be proportional to the inverse number of heat absorption/heat generation quantity of reaction in each region in a longitudinal direction of the catalyst layer. Among the above-mentioned factors, one of the major factors being influential in the optimum change in the thickness of the catalyst layer would be the ultimate conversion rate at the outlet of the starting material gas.

The temperature profile in the catalyst layer varies depending on the reactivity in each step. However, it is possible practically to control temperatures not to damage the catalyst and not to accelerate the deterioration of the catalyst, and to obtain a desired ultimate conversion rate of reaction.

Among the above-mentioned influential factors, the factor related to heat transfer should be considered enough in designing a plate type catalytic reactor. In order to increase the efficiency of removal of heat/application of heat on the catalyst layer, it is preferred to increase the flow rate of the starting material gas. However, it is disadvantageous that the pressure loss becomes large when the gas is passed through the catalyst layer.

When there is a worry that the catalyst deteriorates rapidly at a high temperature even in a common reactor, a technique that an inert material is mixed with the catalyst when it is filled whereby the reactivity of the catalyst is suppressed and the temperature of the catalyst layer is controlled, is employed. Such dilution of the catalyst is also applicable to the plate type catalytic reactor of the present invention.

In a reaction generating a very large reaction heat such as an oxidation reaction, it is necessary to reduce the thickness of the catalyst layer. However, since many pairs of heat transfer plates are located in a reactor, the size of the reactor itself becomes bigger, such being uneconomical. In the present invention too, the service life of the catalyst can be improved by diluting the catalyst with an inert material at the inlet portion of the starting material gas to suppress the generation of a reaction heat.

The dilution of the catalyst is generally carried out stepwise, e.g., at stages of from 2 to 5. The mixing ratio of the inert material is the highest at the inlet portion of the starting material gas while the inert material is not mixed at the outlet of reaction region. The mixing ratio of inert material employed is 0.7 or less in the inlet portion. As the method for controlling the reactivity of the catalyst, a catalyst having different activity may be used other than the method of mixing the inert material. In order to obtain different activities of the catalyst by mixing the inert material or using a different catalyst, it is most preferable that activities of catalyst can continuously be changed from the inlet to the outlet of the starting material gas. However, it is practical to fill stepwise catalysts having different activities in divided sections. Specifically, 2 to 3 kinds of catalysts having different catalytic activities are filled sequentially from the inlet of reaction region.

The reactor of the present invention is preferably used for producing (meth)acrolein or (meth)acrylic acid by an oxidation reaction of propylene or isobutylene with use of a molecular oxygen-containing gas.

The oxidation reaction of propylene or isobutylene generates a large reaction heat. Accordingly, it is absolutely necessary from an economical viewpoint that (meth)acrolein or (meth)acrylic acid is produced with a high yield without a damage of the catalyst by controlling the temperature profile in the catalyst layer filled in the oxidation reactor, and the oxidation catalyst is used stably for a long term. Particularly in a process for producing (meth)acrylic acid by oxidizing (meth)acrolein with molecular oxygen, the activity of the catalyst may be lost in a short period of time due to the characteristics of the used oxidation catalyst when it is exposed to a high temperature of from 300 to 350° C. Further, in recent years, the size of the reactor for producing acrylic acid tends to be increased. With an increase in size of the reactor, the development of an oxidation reactor capable of cooling uniformly the temperature of the catalyst layers is a very important technical point.

A heterogeneous catalyst gas phase oxidation reaction of propylene or isobutylene with molecular oxygen can be performed by using a conventionally known method. In the case of propylene, propylene, air and water vapor or nitrogen are mixed to produce a starting material gas. The concentration of propylene is from 3 to 14 vol %, oxygen is from 6 to 18 vol % and the rest is water vapor, an inert gas such as nitrogen and propane.

The temperature of the heat transfer medium is from 250 to 350° C. and the space velocity (SV) is from 500 to 300 (1/hr) under the normal condition. The reaction pressure is from 150 to 250 kPa. As the heat transfer medium, a molten salt of nitrate mixture (niter) or a polynuclear aromatic type organic heat transfer medium is used in many cases.

The temperature in the catalyst layer should be controlled to from 350 to 400° C. at a maximum. Thus, it was verified that the deterioration of the catalyst could be prevented, the reaction performance could be improved and the yield of acrylic acid and acrolein could be improved.

EXAMPLES

Example 1

In preparing acrylic acid by the oxidation of propylene with molecular oxygen, a catalyst powder having a composition of $Mo_{12}Bi_5Ni_3Co_2Fe_{0.4}B_{0.4}K_{0.1}Si_{24}O_x$ was prepared as a first stage catalyst. The catalyst powder was molded to obtain a ring-shaped catalyst having an outer diameter of 5 mmΦ, an inner diameter of 2 mmΦ and a height of 4 mm.

Similarly, a catalyst powder having a composition of $Sb_{100}Ni_{43}Mo_{35}V_7Nb_3Cu_9Si_{20}O_x$ was prepared as a second stage catalyst. With the catalyst powder, a ring-shaped catalyst having the same shape as the first stage catalyst was prepared. In the above-mentioned compositions, (x) indicates a value given by the oxidation state of each metal oxide.

Two sets of pairs of corrugated heat transfer plates 1 were prepared. Particulars in the shape of these corrugated plates and amounts of the catalysts and an inert are shown in Table 1 described below.

First, the second stage catalyst was filled in amount of 23 liters. Then, the height of the filled catalyst layer was 1.2 m. On the second stage catalyst layer, spherical inert balls (diameter: 5 mmΦ) made of alumina being inactive to reaction were filled in order to adjust the layer height whereby a portion equivalent to the first stage in the reactor was filled. The amount of the filled inert balls was 5 liters.

Similarly, the first stage catalyst and an inert were filled in amounts of 30 liters and 5 liters on the second stage catalyst. The layer height of the first stage catalyst was 1.25 m.

By using 99% purity of propylene containing propane as an impurity, air, nitrogen and water vapor were mixed to be used for the reaction. The mixing ratio was adjusted so that the composition of the gas mixture was propylene (including propane:air:water vapor:nitrogen=7:73.5:10:9.5 vol %. The starting material gas was introduced from the top of the corrugated plate type reactor at a rate of 65 m³ (standard state)/hour. The supply rate of propylene was 8.4 kg/hr.

THERMES 900 (manufactured by Nippon Steel Chemical Co., Ltd.) was introduced as a heat transfer medium into the heat transfer medium flow passages of the corrugated heat transfer plates. The flow rate of the heat transfer medium was 100 m³/hr in the first stage catalyst and 85 m³/hr in the second stage catalyst.

The temperature of the supplied heat transfer medium was adjusted while conversion rates in the respective reaction stages were measured. When the conversion rate in the first stage reaction area was 95%, the temperature of the supplied heat transfer medium showed 287° C. When the acrolein conversion rate in the second stage reaction area was adjusted to 99.5%, the temperature of the heat transfer medium was 260° C.

In the measurement of the temperature of the catalyst layer in the reactor, the highest temperature of the first stage catalyst layer was 359° C. and the highest temperature of the second stage catalyst layer was 297° C. The operation was

TABLE 1

| | Shape of corrugated plate | | | Amount filled (liter) | | Equivalent thickness of catalyst layer (mm) | Throat S (mm) |
| --- | --- | --- | --- | --- | --- | --- | --- |
| | Period of corrugation L (mm) | Height of corrugation H (mm) | Number of corrugation | Catalyst | Inert | | |
| First | 100 | 42 | 8 | 30 | 5 | 16 | 11.5 |
| stage | 100 | 34 | 3 | | | 22 | 18 |
| catalyst | 50 | 14 | 9 | | | 35.5 | 33 |
| Second | 100 | 42 | 8 | 23 | 5 | 16 | 11.5 |
| stage catalyst | 100 | 35 | 7 | | | 21 | 17 |

Here, L and H in the shape of the corrugated plates indicate respectively the width and the length of corrugation shown in FIG. 2. The equivalent thickness of the catalyst layer was obtained from an amount of the filled catalyst and a height of the catalyst layer. Two corrugated plates each being formed by shaping a flat plate having a width of 1 m and a thickness of 0.8 mm were joined to form a heat transfer plate.

Distances ($P_1$ and $P_2$ in FIG. 1) between corrugated heat transfer plates 1 were adjusted to 45 mm to form a reactor and a catalyst was filled in spaces between two heat transfer plates.

continued for a month in this state. As a result, the operation went good without any problem.

Comparative Example 1

The same reactor as in Example was used except that flat plates were used instead of the corrugated plates in the reactor. Two sheets of flat plates each having a thickness of 2 mm, a width of 1 m and a height of 2 m were joined to produce a space of 16 mm therebetween. Heat transfer medium flow passages were provided at the outside of the joined plates.

Reinforcing plates were attached to the plates with intervals of 30 cm at the side of the heat transfer medium flow passages so as to equalize the layer thickness of the catalyst layer and to withstand the pressure of the heat transfer medium.

The same catalyst as in Example 1 was used. When 30 liters of the first stage catalyst was filled, the layer height of the catalyst layer was 1.9 m. On this, an inert was filled serving as a catalyst retainer.

Propylene was oxidized by using a reaction gas having the same composition as Example 1 at the same flow rate as Example 1. The flow rate of the heat transfer medium was adjusted to have the same linear velocity in the flow passages as Example 1.

In the measurement of the conversion rate of propylene, there was 95% at a heat transfer medium temperature of 315° C. The thermometer inserted in the catalyst layer showed 408° C. at the highest temperature of the catalyst layer.

The reaction was continued for a week while reaction conditions were fixed. As a result, the highest temperature of the catalyst layer decreased and the conversion rate of propylene decreased gradually. In order to maintain the conversion rate of propylene, the temperature of the heat transfer medium had to be further increased.

Example 2 and Comparative Example 2

Tests of filling the first stage catalyst were carried out by using the same corrugated heat transfer plate type reactor as Example 1 and the same flat type reactor as Comparative Example 1 except that the height of the heat transfer plates was 3.05 m.

The first stage catalyst produced in Example 1 was filled into respective oxidation reactors from their tops. A horizontally elongated funnel-like device was attached to the top of the respective reactors so that the catalyst did not run over the reactors.

Into each reactor, the catalyst put in a beaker of 1 liter volume was introduced in a time of about 6 seconds. This operation was conducted three times. After the filling of 3 liters of catalyst, the catalyst was discharged from a lower part of the reactor. In the discharged catalyst, pieces of cracked catalyst were separated with a sieve (10 meshes) and by visual check to obtain the ratio. This operation was repeated three times. Results are shown in Table 2.

can be weakened until the catalyst reaches the lower portion of the reactor because it falls hitting the projected portions of thin corrugated plates.

INDUSTRIAL APPLICABILITY

According to the present invention, the highest temperature of the catalyst layer can be suppressed to be low and the performance of reaction can be improved. In the plate type catalytic reactor of the present invention, a reduction in the performance of reaction due to the deterioration of the catalyst and a change in the temperature profile are not found even after a long term continuous reaction.

In the plate type catalytic reactor of the present invention, the flow of a starting material gas is disturbed by the presence of projected or recessed surfaces provided in the corrugated plates to increase the heat transfer efficiency of the starting material gas. As a result, the thickness of the catalyst layer can be increased and the reactor can be made compact. Further, when the catalyst is filled in the catalyst layer, the catalyst falls hitting the projected and recessed surface parts of the corrugated plates whereby the falling speed can be reduced. Accordingly, there causes less breakages of the catalyst due to the falling impact and less deterioration of the catalyst.

The entire disclosure of Japanese Patent Application No. 2002-376639 filed on Dec. 26, 2002 including specification, claims, drawings and summary is incorporated herein by reference in its entirety.

What is claimed is:

1. A plate type catalytic reactor, comprising:
a plurality of heat transfer plates, each formed of two sheets of corrugated plates joined to each other and each having a plurality of heat transfer medium flow passages, said plates being arranged so that projected surface parts and recessed surface parts of the corrugated plates of adjacent heat transfer plates are opposed to each other to form a catalyst layer, wherein the term "catalyst layer" is defined as the space between a pair of heat transfer plates and adjacent pairs of heat transfer plates, wherein the catalyst fills said space therebetween, wherein a circular or elliptic arc shape that is formed in the corrugated plates is changed to increase the thickness of the catalyst layer from the inlet toward the outlet for a starting material gas fed to the catalyst layer.

TABLE 2

|  |  | Example 2 | | | Comparative Example 2 | | |
|---|---|---|---|---|---|---|---|
|  |  | Type of reactor | | | | | |
|  |  | Corrugated heat transfer plate type reactor | | | Flat heat transfer plate type reactor | | |
| Amount of catalyst filled | g | 2,160 | 2,182 | 2,149 | 2,171 | 2,184 | 2,145 |
| Amount of catalyst cracked | g | 3.2 | 4.1 | 4.3 | 108.5 | 117.9 | 128.7 |
| Ratio of cracking | % | 0.15 | 0.19 | 0.20 | 5.0 | 5.4 | 6.0 |
| Ratio of cracking in average | % | 0.18 | | | 5.5 | | |

From the results in Table 2, it was found that when a catalyst was filled in the reactor of the present invention, the possibility of cracked catalyst due to the dropping impact was very small.

This can be considered as follows. In the reactor using corrugated heat transfer plates according to the present invention, when the catalyst is introduced in it, the dropping impact 2. The plate type catalytic reactor according to claim 1, wherein a plurality of corrugated heat transfer plates are arranged in a radial pattern, the starting material gas is fed from the inner side to the outer side of the catalyst layer, and the heat transfer medium is fed into the flow passages of the corrugated heat transfer plates so as to form a cross current flow with respect to the starting material gas.

3. A method of conducting a catalytic reaction, comprising:
conducting the reaction in the plate type catalytic reactor of claim 1, wherein the heat transfer medium flow passages of the corrugated heat transfer plates are arranged to extend vertically so that the heat transfer medium supplied from the downward flow upward and at least a portion of the heat transfer medium is boiled in the heat transfer medium flow passages.

4. A method of conducting a catalytic reaction, comprising:
conducting the reaction in the plate type catalytic reactor of claim 2, wherein the heat transfer medium flow passages of the corrugated heat transfer plates are arranged to extend vertically so that the heat transfer medium supplied from the downward flow upward and at least a portion of the heat transfer medium is boiled in the heat transfer medium flow passages.

5. A method of conducting a catalytic reaction, comprising:
conducting the reaction in the plate type catalytic reactor of claim 1, wherein the heat transfer medium is fed into the reactor so as to form a cross current flow with respect to the starting material gas.

6. A method of conducting a gas phase catalytic reaction, comprising:
oxidizing propylene or isobutylene in the presence of a molecular oxygen-containing gas in the plate type catalytic reactor according to claim 1 to produce (meth)acrolein and (meth)acrylic acid.

7. A method of conducting a gas phase catalytic reaction, comprising:
oxidizing propylene or isobutylene in the presence of a molecular oxygen-containing gas in the plate type catalytic reactor according to claim 2 to produce (meth)acrolein and (meth)acrylic acid.

8. A method of conducting a gas phase catalytic reaction, comprising:
oxidizing (meth)acrolein in the presence of a molecular oxygen-containing gas in the plate type catalytic reactor according to claim 1 to produce (meth)acrylic acid.

9. A method of conducting a gas phase catalytic reaction, comprising:
oxidizing (meth)acrolein in the presence of a molecular oxygen-containing gas in the plate type catalytic reactor according to claim 2 to produce (meth)acrylic acid.

10. The method of claim 3, wherein said catalytic reaction is conducted by passing a fluid reaction material through the catalyst layers between pairs of corrugated sheets, whereby heat is exchanged between the reaction fluid and a heat transfer medium circulating through said passages defined by pairs of corrugated sheets, thereby resulting in boiling of at least a portion of the heat transfer medium in the heat transfer medium flow passages.

11. The method of claim 4, wherein said catalytic reaction is conducted by passing a fluid reaction material through the catalyst layers between pairs of corrugated sheets, whereby heat is exchanged between the reaction fluid and a heat transfer medium circulating through said passages defined by pairs of corrugated sheets, thereby resulting in boiling of at least a portion of the heat transfer medium in the heat transfer medium flow passages.

* * * * *